US00PP08800P

United States Patent [19]

van der Velden

[11] Patent Number: Plant 8,800

[45] Date of Patent: Jun. 21, 1994

[54] CORDYLINE PLANT—PICOLO VARIETY

[75] Inventor: Petrus J. L. van der Velden, Sint-Oedenrode, Netherlands

[73] Assignee: Handelskwekerij van der Velden B.V., Sint-Oedenrode, Netherlands

[21] Appl. No.: 16,998

[22] Filed: Feb. 12, 1993

[51] Int. Cl.[5] ..... A01H 5/00

[52] U.S. Cl. ..... Plt./88.11

[58] Field of Search ..... Plt. 88.1, 88.11

*Primary Examiner*—James R. Feyrer

*Attorney, Agent, or Firm*—Burns, Doane, Swecker & Mathis

[57] ABSTRACT

A new and distinctive variety within the Liliaceae family, botanically known as *Cordyline fruticosa* is provided. The new variety originated as a mutation of the Red Edge variety (non-patented in the United States) and exhibits a more compact growth habit (as illustrated) than its parent. The internode lengths of the new variety are less as are the leaf lengths and widths. The new variety serves well as an attractive ornamental pot plant and has been named the Picolo variety.

2 Drawing Sheets

SUMMARY OF THE INVENTION

The new variety was discovered as a mutation of unknown causation while growing among plants of the Red Edge variety of *Cordyline fruticosa* growing in the nursery of Handelskwekerij van der Velden B. V. located at Sint-Oedenrode, The Netherlands. The parent Red Edge variety is sometimes known as the Babydoll variety in the United States and is non-patented in the United States. The parent Red Edge variety is well known to the trade not to exhibit dwarf growth characteristics and currently bears auction Code No. 9183 of the Flower Council of Holland. The new variety was discovered among plants of the Red Edge variety which were being subjected to controlled growing conditions during the course of a research program involving the application of a C.C.C. growth retardant in an effort to shorten leaves so as to minimize undesirable leaf tip burning. A single plant was discovered having the characteristics of the new variety of the present invention. Had this new variety not been discovered and preserved, it would have been lost to mankind. It is unknown whether the application of the growth retardant had any influence in the creation of the new mutation of the present invention. It is considered to be doubtful that the growth retardant can be considered to have influenced the creation of the permanent mutation of the present invention since such result is not known to have ever been reported in the past. Accordingly, the new variety resulted from judicious selection among a large number of plants of the Red Edge parent variety as described herein.

It was found that the following combination of characteristics is exhibited by the new variety of *Cordyline fruticosa* when grown under standard greenhouse conditions:

(a) exhibits a bi-colored leaf coloration that is substantially identical to that of the Red Edge variety when grown under comparable growing conditions,
(b) exhibits a dwarf growth habit that is absent in the Red Edge variety,
(c) exhibits leaves that better resist leaf tip burning than the leaves of the Red Edge variety, (d) exhibits shorter internode lengths, shorter leaf lengths and shorter leaf widths than the Red Edge variety,
(e) exhibits a shorter leaf stalk that tends to be more gutter-shaped than that of the Red Edge variety, and
(f) is particularly well suited for growing as an ornamental pot plant.

The new variety has been continuously evaluated for its performance since the time of its initial discovery. The characteristics of the new variety have been found to be stably manifest in succeeding generations following asexual propagation by cuttings and tissue culture carried out at The Netherlands and at Costa Rica. A distinctive new cultivar is provided for growing indoors as an attractive ornamental pot plant.

The new dwarf Cordyline plant of the present invention has been named the Picolo variety.

BRIEF DESCRIPTION OF THE PHOTOGRAPH

FIG. 1 shows three typical plants of the new cultivar at an age of approximately three months. The plants were produced by the rooting of cuttings, and were grown in standard potting soil in a greenhouse at Sint-Oedenrode, The Netherlands. The distinctive dwarf habit of the new Picolo variety is apparent.

FIG. 2 shows a typical plant of the new cultivar at the left and a typical plant of the Red Edge cultivar at the right. Each plant was formed from a rooted cutting formed over a period of three weeks while maintained at 25° C. in an environment of 95 percent relative humidity. The rooted plants subsequently were grown for approximately 13 weeks at 20° C. with uncontrolled humidity. The distinctive dwarf growth habit of the new Picolo variety when compared to the Red Edge variety is apparent. The Picolo plant exhibits internode lengths of approximately 9 to 11 mm., and the Red Edge plant exhibits internode lengths of approximately 12 to 16 mm.

DETAILED DESCRIPTION OF THE NEW VARIETY

The following description of the new variety of *Cordyline fruticosa* is based upon the observation of plants growing under standard greenhouse conditions at Sint-Oedenrode, The Netherlands. Colors sometimes are identified with reference to the R.H.S. Colour Chart of The Royal Horticultural Society, London. In other instances, common color terms are used which are to be accorded their ordinary dictionary significance.

The bi-colored leaf coloration of the new variety is substantially the same as that of the parent Red Edge variety. The leaves exhibit a purple margin and a dark green center (as illustrated). The inner configuration and depth of the purple leaf margin commonly is somewhat irregular. The upper leaf margin coloration commonly approximates Red-Purple Group 60B, and upper leaf center coloration commonly approximates Green Group 139A. A number of conditions can influence leaf coloration as will be apparent to those skilled in plant science. For instance, more exposure to light tends to intensify the leaf coloration. Other factors that can influence leaf coloration are low humidity in the surrounding environment, a high potassium level in the soil, a low level of nitrogen in the fertilizer, and exposure to low temperatures. Also, very young leaves initially may exhibit a cream-colored banding on the margins of the upper surfaces prior to the full development of the leaf coloration described herein. The midrib on the underside of the leaves commonly is dark purple. The mature leaves commonly arch upward from the point of attachment and possess downwardly curved tips. The leaf margins commonly curve slightly upwards. The leaves tend to be somewhat lanceolate in configuration (as illustrated). Also, the leaves of the new variety tend to exhibit a propensity to undergo less leaf tip burning than the Red Edge variety. Accordingly, the attractiveness of the overall plant is further enhanced because of this important characteristic. Such leaves of the new variety commonly measure aproximately 7 cm. in length and approximately 2.5 cm. in width.

Figure 1:
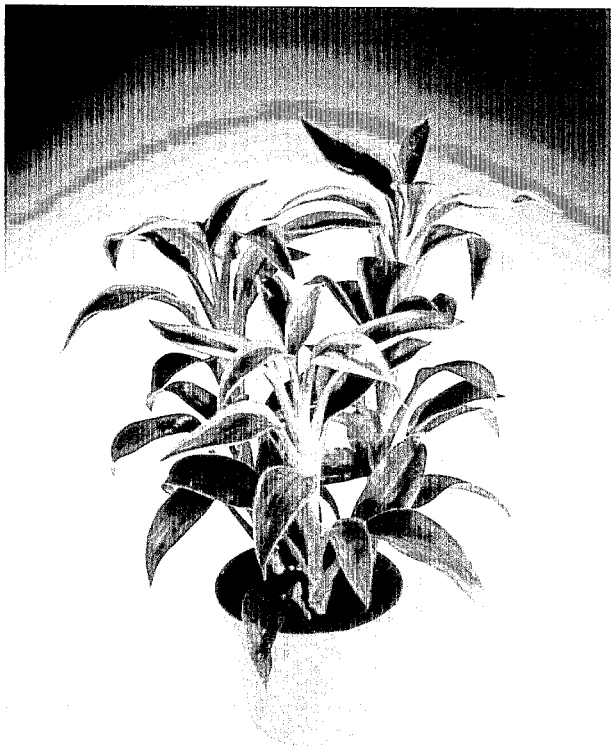
Figure 2:
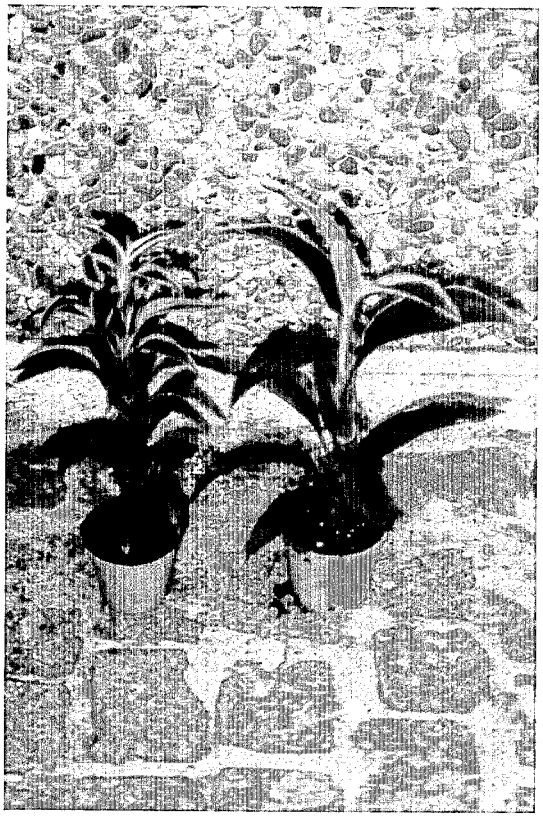

The new variety exhibits a dwarf growth habit which can be used to readily distinguish it from its parent Red Edge variety that is recognized to exhibit a standard growth habit. For instance, the three-month-old Picolo plant illustrated in FIG. 1 has a height of approximately 15 cm and a maximum width of approximately 10 cm. A comparable plant of the parent Red Edge variety would not exhibit the illustrated dwarf growth habit and commonly would have a height of approximately 18 cm and a width of approximately 15 cm when grown under the same conditions.

The new variety exhibits generally shorter internode lengths than the parent Red Edge variety. It has been found that the internode lengths are influenced to at least some degree by the location of the stem, the growing season, the light level, and the fertilizer level. Internode lengths for the Picolo variety have been found to range from approximately 1.5 to 11 mm., and for the Red Edge variety from approximately 2 to 16 mm. Also, the leaves of the new variety generally are smaller than those of the Red Edge variety. For instance, the leaves of the new variety commonly measure approximately 8 cm inches in length and approximately 20 mm. in width while the leaves of the Red Edge variety commonly measure up to approximately 10 cm inches in length and approximately 30 mm. in width.

The leaf stalk of the new variety tends to be shorter and of a more pronounced gutter shape than that of the parent Red Edge variety. The leaf stalk commonly measures approximately 3 cm. in length. In contrast, the leaf stalk length of the Red Edge variety commonly is approximately 4 cm. in length. The leaf stalk of the new Picolo variety commonly is near Greyed-Purple Group 187A to Brown Group 200A in coloration, and commonly bears a margin having a width of approximately 2 mm. that approaches the coloration of Red-Purple Group 60B to Greyed-Purple Group 185B.

When the leaves of the Picolo variety have just dropped and the stem is exposed to direct light for the first time, the stem coloration commonly is a pinkish-white, Red Group 36A. After some time, such a leaf stalk coloration commonly will change to approximately Red-Purple Group 71A.

The Picolo variety does not form aerial roots under all circumstances, and the formation of such roots appears to be influenced by the size and age of the plant. For instance, larger mother plants of the Picolo variety have been observed to exhibit adventitious roots.

The Picolo variety shows some intendency to branch; however, the tendency to branch appears to be somewhat less than that of the Red Edge variety.

No flowers have been observed on plants of the Picolo variety to date. It is not known at this time whether the Picolo variety will bloom when plants are fully mature. It is possible that the continued removal of cuttings from older plants of the Picolo variety observed to date has precluded blooming.

The Picolo variety is well suited for service as an ornamental pot plant when grown indoors. When grown outdoors it is recommended that the plant not experience temperatures below approximately 5° C. The plant requires full light, but bright sunlight should be avoided during the spring and summer. The soil in which the plant is grown should be kept moderately moist during growth and may be allowed to dry slightly between each application of water.

I claim:

1. A new and distinct variety of *Cordyline fruticosa* having the following combination of characteristics:

(a) exhibits a bi-colored leaf coloration that is substantially identical to that of the Red Edge variety when grown under comparable growing conditions,
(b) exhibits a dwarf growth habit that is absent in the Red Edge variety,
(c) exhibits leaves that better resist leaf tip burning than the leaves of the Red Edge variety,
(d) exhibits shorter internode lengths, shorter leaf lengths and shorter leaf widths than the Red Edge variety,
(e) exhibits a shorter leaf stalk that tends to be more gutter-shaped than that of the Red Edge variety, and
(f) is particularly well suited for growing as an ornamental pot plant;

substantially as illustrated as described.

* * * * *